(12) United States Patent
Virtanen et al.

(10) Patent No.: US 12,161,483 B2
(45) Date of Patent: Dec. 10, 2024

(54) REATTACHABLE SpO2 SENSOR WITH AMBIENT LIGHT ATTENUATION

(71) Applicant: GE Precision Healthcare LLC, Wauwatosa, WI (US)

(72) Inventors: Juha P. Virtanen, Helsinki (FI); Emma E. Hellmann, Espoo (FI); Terho Pulliainen, Helsinki (FI)

(73) Assignee: GE Precision Healthcare LLC, Wauwatosa, WI (US)

( * ) Notice: Subject to any disclaimer, the term of this patent is extended or adjusted under 35 U.S.C. 154(b) by 879 days.

(21) Appl. No.: 17/094,322

(22) Filed: Nov. 10, 2020

(65) Prior Publication Data
US 2022/0146494 A1 May 12, 2022

(51) Int. Cl.
*A61B 5/00* (2006.01)
*A61B 5/1455* (2006.01)

(52) U.S. Cl.
CPC .......... *A61B 5/6826* (2013.01); *A61B 5/6833* (2013.01); *A61B 5/14552* (2013.01)

(58) Field of Classification Search
CPC ............ G01N 33/4925; A61B 5/14552; A61B 5/6826; A61B 5/6833
See application file for complete search history.

(56) References Cited

U.S. PATENT DOCUMENTS

| | | | |
|---|---|---|---|
| 4,825,879 A * | 5/1989 | Tan ...................... | A61B 5/6826 600/490 |
| 7,486,977 B2 | 2/2009 | Sweitzer et al. | |
| 10,589,044 B2 | 3/2020 | Sherman et al. | |
| 2011/0301444 A1* | 12/2011 | Al-Ali .................. | A61B 5/6826 600/344 |
| 2020/0246566 A1 | 8/2020 | Sherman et al. | |

OTHER PUBLICATIONS

International Application No. PCT/US2021/058294 filed Nov. 5, 2021—International Search Report and Written Opinion issued on Jan. 28, 2022; 13 pages.

* cited by examiner

*Primary Examiner* — Eric F Winakur
*Assistant Examiner* — Abid A Mustansir

(57) ABSTRACT

A sensing device for acquiring data via a finger. The device includes a wrap having a central portion with a tip wing, a first side wing, and a second side wing each extending therefrom. The wrap has an exterior side and an opposite finger side that faces towards the finger. An electronics system is coupled to the wrap and has a sensor configured to acquire the data from the finger. An adhesive is configured to adhere the sensing device to the finger. First and second attachment portions are positioned on finger side of the first side wing and on the exterior side of the second side wing, respectively, where the first and second attachment portions removably attach to each other to non-adhesively secure the wrap around the finger.

18 Claims, 5 Drawing Sheets

REATTACHABLE SpO2 SENSOR WITH AMBIENT LIGHT ATTENUATION

FIELD

The present disclosure generally relates to a reattachable SpO2 sensor with ambient light attenuation, and more particularly to reattachable SpO2 sensor incorporating multiple modes of attachment to enable effective reattachment while providing good ambient light attenuation.

BACKGROUND

Pulse oximetry is patient monitoring process known in the art for measuring the oxygen saturation within a blood stream, and particularly non-invasively. Specifically, pulse oximeters are devices configured to measure the peripheral oxygen saturation (SpO2) within a patient's bloodstream, which can provide invaluable information about the patient's health. Exemplary sensors known in the art can be classified as either reflective or transmissive sensor types. In each case, the pulse oximeter transmits light (typically of two wavelengths) through a body part, such as a finger or toe, whereby the light is then detected via a photodetector. Different materials absorb light at differing rates at the differing wavelengths. Therefore, it is possible to determine peripheral oxygen saturation using the detected light since oxygen in the bloodstream absorbs light differently than other materials, such as skin, bone, muscle, fat, and fingernail, for example. In the case of a transmissive configuration, the light transmission device and photodetector are positioned on opposing sides of a body part, for example where the light passes straight through a finger or toe. In contrast, reflectance pulse oximeters detect the light reflecting back from the body part, or in other words where the photodetector is not be on an opposing side of the body part from the transmitter.

It is critical for the accuracy for pulse oximeters that the device is provided in good contact with the body part. Likewise, it is important that ambient light is blocked so that the light detected at the photodetector is effectively exclusively from the transmitter.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

One embodiment of the present disclosure generally relates to a sensing device for acquiring data via a finger. The device includes a wrap having a central portion with a tip wing, a first side wing, and a second side wing each extending therefrom. The wrap has an exterior side and an opposite finger side that faces towards the finger. An electronics system is coupled to the wrap and has a sensor configured to acquire the data from the finger. An adhesive is configured to adhere the sensing device to the finger. First and second attachment portions are positioned on finger side of the first side wing and on the exterior side of the second side wing, respectively, where the first and second attachment portions removably attach to each other to non-adhesively secure the wrap around the finger.

Another embodiment generally relates to a sensing device for acquiring data via a finger. The device includes a wrap having a central portion with a tip wing, a first side wing, and a second side wing each extending therefrom. The central portion defines a central opening therein. The wrap has an exterior side and an opposite finger side that faces towards the finger. An electronics system is coupled to the wrap and has a sensor configured to acquire the data from the finger. An adhesive is configured to adhere the sensing device to the finger. First and second attachment portions are positioned on finger side of the first side wing and on the exterior side of the second side wing, respectively, where the first and second attachment portions removably attach to each other to non-adhesively secure the wrap around the finger. A canopy extends upwardly from the exterior side of the central portion, where the canopy defines an interior volume accessible through the central opening in the central portion, and where the electronics system has a stacked portion that is at least partially positioned within the canopy.

Another embodiment generally relates to a method for securing a medical device on a finger. The method includes wrapping a wrap of the medical device around the finger, where the wrap has a central portion with a tip wing, a first side wing, and a second side wing each extending therefrom. The wrap has an adhesive thereon configured to be adhered to the finger, where the first side wing has a first attachment portion coupled thereto, and the second side wing has a second attachment portion coupled thereto. The method further includes adhering the wrap to the finger via the adhesive on the wrap. The method further includes engaging the first attachment portion on the first side wing to the second attachment portion on the second side wing. The first attachment portion and the second attachment portion are engaged non-adhesively, and where the medical device is secured to the finger by both the adhesion on the wrap and by the engagement of the first attachment portion and the second attachment portion.

Another embodiment generally relates to an SpO2 sensing device securable on a finger. The SpO2 sensing device includes an elastic wrap having a central portion with an central opening defined therein, where a tip wing, a first side wing, and a second side wing each extend from the central portion, and where the wrap has an exterior side and an opposite finger side facing towards the finger. A canopy extends upwardly from the exterior side of the central portion and defining an interior volume therein. A first sealing layer is coupled to the interior side of both the central portion and tip wing, where an opening is defined through the first sealing layer. An electronics system has a canopy side facing the canopy, a finger side facing the finger, and a connector side between the canopy side and the finger side, where the electronics system extends through the opening in the first sealing layer and through the central opening in the wrap such that the canopy side is positioned within the canopy. The electronics system further includes a carrier board and transmitter and a receiver that extend away from the carrier board towards the finger. A second sealing layer is coupled to the carrier board of the electronics system, where openings are defined through the second sealing layer into which the transmitter and the receiver extend, respectively. An adhesive layer is coupled to the second sealing layer at an exterior side, the adhesive layer also having a finger side opposite the exterior side that has adhesive to retain the device on the finger. First and second attachment portions are positioned on finger side of the first side wing and on the exterior side of the second side wing, respectively, where the first and second attachment portions together comprise a hook and loop fastener removably attachable to secure the wrap around the finger.

Various other features, objects and advantages of the disclosure will be made apparent from the following description taken together with the drawings.

BRIEF DESCRIPTION OF THE DRAWINGS

The present disclosure is described with reference to the following Figures.

DETAILED DISCLOSURE

Figure 1:
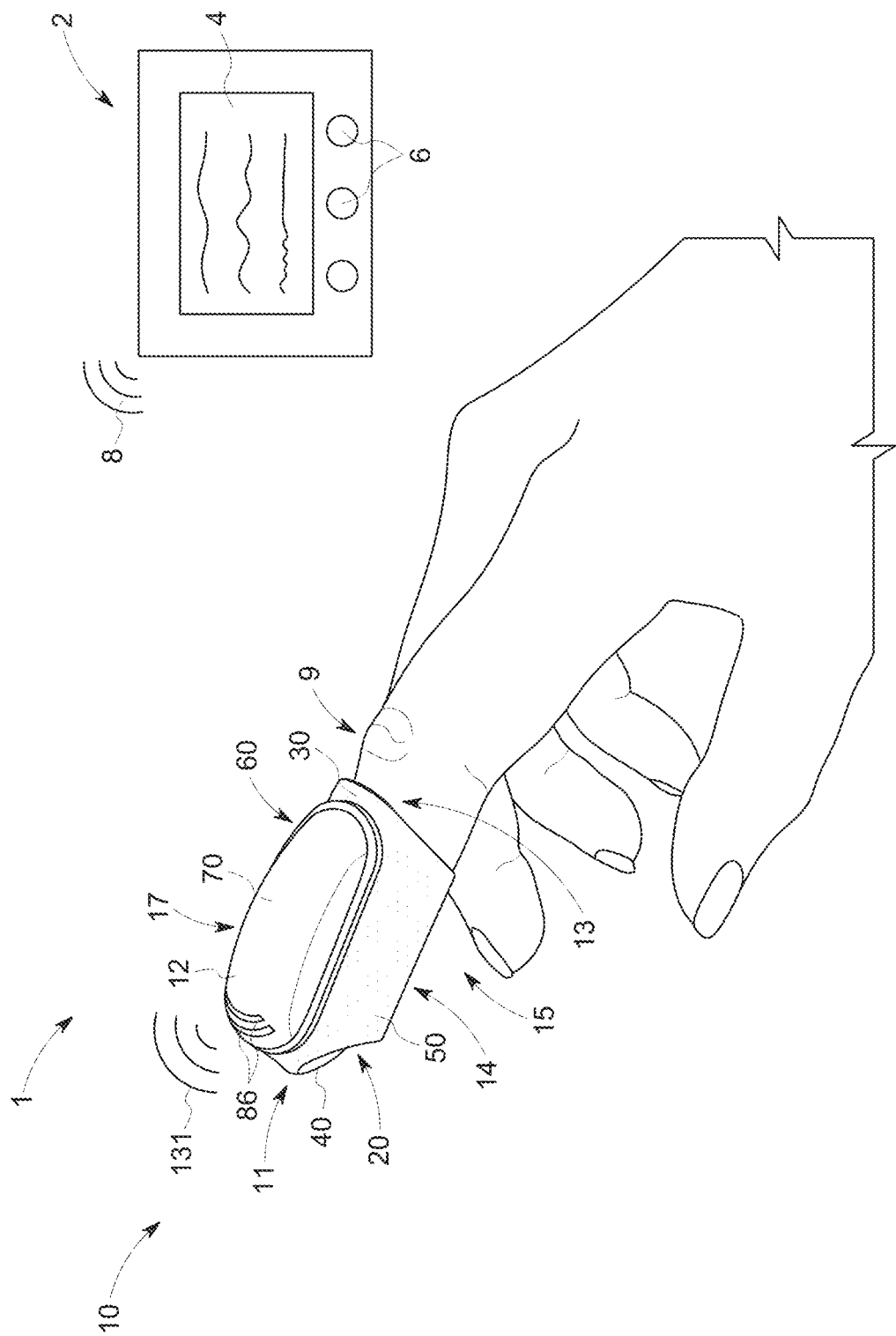
FIG. 1 is an isometric top view of an exemplary sensor device provided on the finger of a patient according to the present disclosure.

Through experimentation and development, the inventors have recognized multiple problems with SpO2 sensor devices presently known in the art, both respect to usability, and the quality and accuracy of data being produced. In particular, the inventors have recognized the importance of SpO2 sensors being configured to be tightly fixed to a body part, such as a finger, which improves light transmission and helps reduce the detection of ambient light. The challenge of achieving good fixation is further exacerbated as SpO2 devices become wireless, allowing patients to become more mobile and active. The inventors have recognized that issues further arise with respect to the durability of single-use detectors being used over longer periods of time, in certain cases 72 hours or longer. In these extended duration situations, it is often necessary to periodically remove the sensor, for example when the patient washes their hands. However, the inventors have recognized that sensor devices presently known in the art do not do well being detached and reattached several times. The adhesives start to fail and/or the wrap material becomes damaged, leading to poor engagement with the skin that results in decreased comfort and degraded quality of the outputted data.

With respect to sensor devices presently known in the art, the inventors have recognized the following shortcomings. Certain sensors are of a "rubber boot" type configured to be reusable. However, the inventors have recognized that these devices are physically heavy due to the use of the thick elastomer, resulting in patient discomfort and poor resultant data. Fixation to the finger is also inadequate, as these rubber boot type sensors are not well suited for a full range of patient sizes (e.g., finger sizes), which can range greatly by weight, gender, and age, for example. In addition to poor fixation or pressure on the finger, the rubber boot style also provides poor breathability, once again degrading data output due to extensive sweating, and further worsening fixation.

Clip-type sensors also exist but are mechanically complex and thus are not suited for single-use devices (e.g., GE Healthcare's® TruSignal Finger Sensor TS-F-D).

Bandage type single-use sensors have also become common, which generally consist of a textile-like wrap with an adhesive surface for bonding to the skin (for example, GE Healthcare's® TruSignal Adult Adhesive Wrap sensor TS-AAW). These designs tend to lose adhesion when being detached and reattached. Additionally, the wraps of presently known devices are narrow and provide only minimal ambient light attenuation. GE Healthcare® produces an airplane-type disposable sensor (for example, GE Healthcare's® TruSignal Adult/Pediatric sensors (TS-AP having a wing that wraps over a fingertip, and two identical side wings that wrap around the finger) that while covering the finger well and providing good ambient light attenuation is difficult to provide and maintain controlled pressure on the finger.

As will become apparent, the presently disclosed sensor devices solve many of the problems mentioned above, as well as providing other improvements for single-use sensors. Among these, the disclosed sensor is configured to be tightly (but adjustably) fixed to the finger, and to remain effective despite being attached and detached several times during an extended period of use, for example 72 hours or more. The disclosed sensors provide adequate pressure on the fingertip for optimal performance, and also provide good attenuation of ambient light.

The inventors have recognized that attenuation has become further problematic as patients increasingly use mobile devices while being monitored by an SpO2 sensing device. In this case, substantial light may be emitted from these mobile devices in close proximity to the SpO2 sensing devices, effecting the accuracy of the outputted data since not all detected light is coming from the patient. Moreover, the disclosed sensors are lightweight, provide for a minimal amount of materials for disposing, refurbishing, and/or recycling (e.g., of batteries), and allow for breathability such that extensive sweating does not occur.

It will be recognized that while the present disclosure principally refers to SpO2 devices, the devices and methods disclosed herein are also applicable for other devices being coupled to a subject (which is not limited to humans, for example also including animals), and not limited to placement on a finger (for example, including wrists, arms, ankles, legs, toes, or an entire foot for a neonatal infant). For example, the disclosed methods and devices may be adapted for single-use blood pressure monitoring, blood glucose monitoring, drug delivery infusion devices, and other medical or non-medical devices. Likewise, while the present disclosure generally refers to communication with the device being wireless, wired configurations are also anticipated.

FIG. 1 depicts an exemplary embodiment of a sensing device 10 according to the present disclosure. As shown, the overall system 1 includes the sensing device 10 for obtaining SpO2 data from a finger 9 of a patient. The sensing device 10 communicates via a wireless communication device and antenna 131 with a central receiver 2 in a manner known in the art. For example, wireless communication may be provided via Bluetooth®, wi-fi, or other long, short, or medium range wireless protocols known in the art. In the example shown, the central receiver 2 has a display 4 and controls 6 and communicates with the sensing device 10 via wireless connections 8 therebetween.

The sensing device 10 extends from a tip side 11 aligned with the tip of the finger 9, to a knuckle side 13, as well as a left side 15 and right side 17. A top 12 is oriented above the finger 9, with an opposite bottom 14 on the underside of the finger. The sensing device 10 is held in place on the finger 9 by a wrap 20 (also referred to as a cover), which is discussed further below. A canopy 70 extends above the wrap 20 and contains at least a portion of the electrical components for the sensing device 10 therein, which are discussed further below. The canopy 70 provides the space for these electrical components to extend above the wrap 20, while also protecting them from moisture, impact, and/or other damage or interference.

Figure 2:
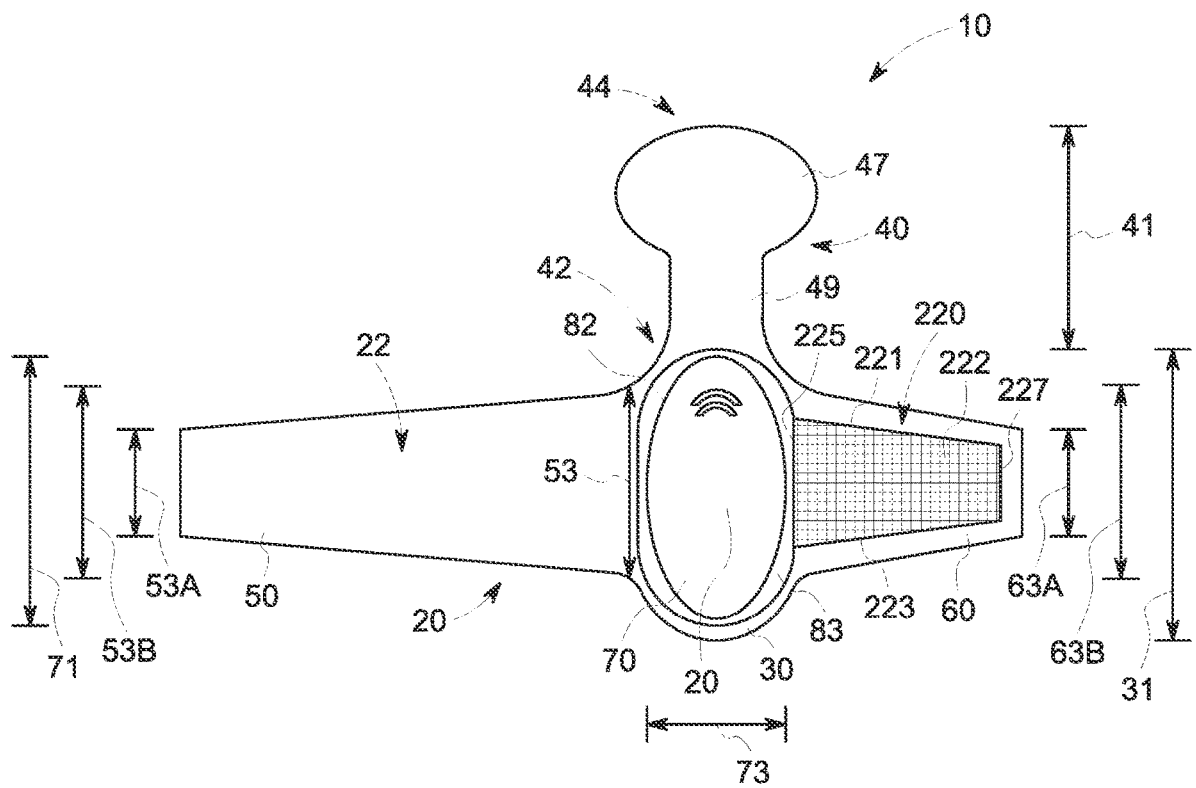
FIGS. 2 and 3 are top and bottom views, respectively, of portions of the device shown in FIG. 1.
Figure 3:
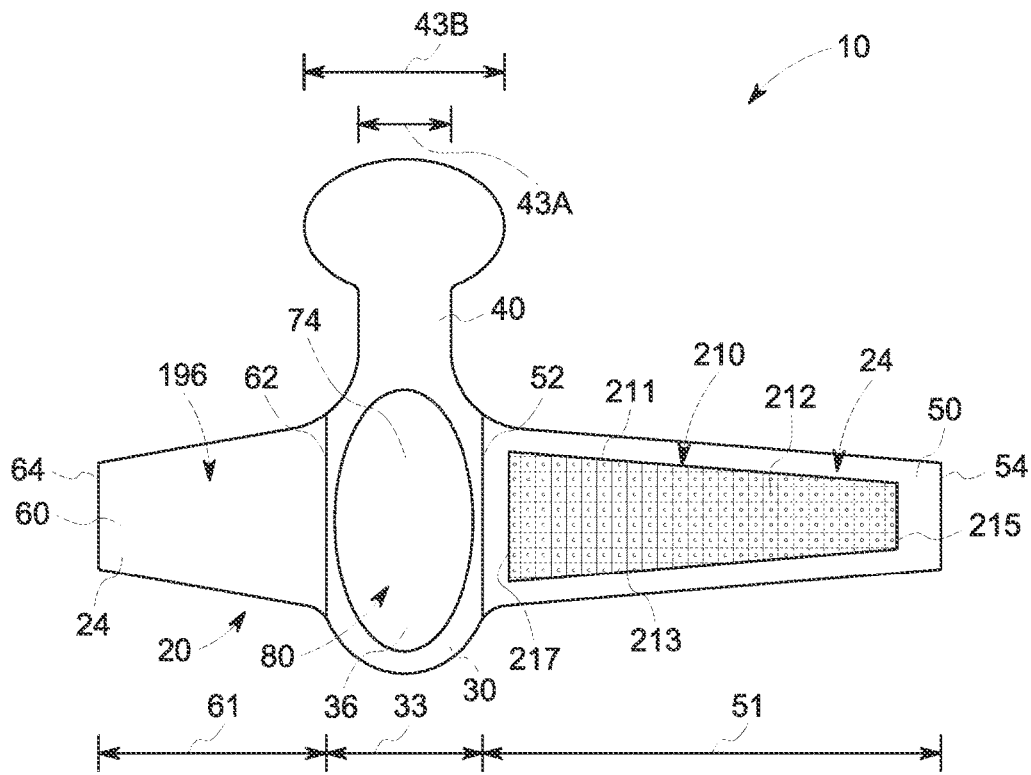

FIGS. 2 and 3 depict the wrap 20 and canopy 70 of the sensing device 10 of FIG. 1 from top and bottom views, respectively, without electrical components installed therein. The wrap 20 has an exterior side 22 opposite a finger side 24, whereby the finger side 24 is configured to contact the finger 9 of the patient in use. The wrap 20 is formed by a central portion 30 having a length 31 and a width 33 and defining a central opening 36 therein. A tip wing 40 having a bulb 47 and an extension 49 extends from the central portion 30 of the wrap 20. The tip wing 40 is configured to wrap over the tip of the finger 9 such that a portion of the extension 49 remains above the finger (e.g., on the fingernail) with the bulb 47 opposing the portion of the extension 49 on the underside of the finger 9. The tip wing 40 has a base end 42 and distal end 44 extending a length of 41 therebetween, and also widths 43A, 43B corresponding to the extension 49 and bulb 47. It will be recognized that while the bulb 47 has a greater width 43B than the width 43A of the extension 49, this is not required, and other configurations are anticipated by the present disclosure. The wrap 20 may be formed of materials presently known in the art, including woven or non-woven fabrics, films, tapes, or foams, for example.

As also shown in FIGS. 2 and 3, first and second side wings 50, 60 also extend from the central portion 30 in opposing directions from each other. In the embodiment shown, the first side wing 50 has a base end 52 and distal end 54 and extends a length 51 therebetween. The first side wing 50 has widths 53A, 53B and is shown to be extending from the central portion 30 approximately 90° apart from the extension of the tip wing 40. Similarly, the second side wing 60 has a base end 62 and distal end 64 and extends a length 61 therebetween. The second side wing 60 has widths 63A, 63B, which like the widths 53A, 53B of the first side wing 50 taper downwardly as the second side wing 60 and first side wing 50 extend away from the central portion 30. The inventors have recognized that wrapping the wrap 20 around the finger 9 on three sides as presently shown is particularly effective at attenuating ambient light, as well as fixating the device.

It will be recognized that while the present disclosure principally focuses on wraps having three wings that wrap around a finger, other numbers of wings are also anticipated, whether for use with fingers or other parts of a subject. For example, other embodiments according to the present disclosure include two side wraps without a tip wing, a single side wrap that attaches to itself (with or without a tip wing), and other configurations (e.g., multiple side wings resembling a butterfly bandage, with or without a tip wing), to name a few.

In the embodiment of FIGS. 2 and 3, an adhesive 196 is provided on the finger side 24 of the wrap 20, particularly on the second side wing 60, to assist in fixating the sensing device 10 on the finger 9. This embodiment also features additional adhesive 196 provided over the central portion 30, as discussed further below. In addition to these adhesives 196, FIGS. 2 and 3 depict an attachment system including the first attachment portion 210 and second attachment portion 220 configured to releasably engage each other, which in the present example are hook and loop type fasteners (e.g., Velcro®). The first attachment portion 210 is affixed to the finger side 24 of the wrap 20 particularly on the first side wing 50, and in the present example is the "loop" portion of the attachment system as this side faces the finger 9 of the patient. Likewise, the second attachment portion 220 is affixed to the exterior side 22 of the wrap 20, particularly on the second side wing 60, and in the present case constitutes the "hook" that engages the loops. It will be recognized that different types of fasteners (e.g., "touch" or 3M®'s "dual lock" fasteners) may be used as the first attachment portion 210 and second attachment portion 220, as well as alternating the positions of these first and second attachment portions 210, 220.

In the examples shown in FIGS. 2 and 3, the first attachment portion 210 has a tip side 211, knuckle side 213, left side 215, and right side 217. An exterior side 212 is configured to engage with the second attachment portion 220, and an interior side (not labeled) is configured to be attached to the wrap 20, for example using an adhesive. Exemplary adhesives available in the market include double coated polyethylene tape, acrylic adhesive tape, and others known in the art. In a similar manner, the second attachment portion 220 extends between a tip side 221 and a knuckle side 223, and between a left side 225 and a right side 227. An exterior side 222 is configured to engage with the first attachment portion 210 in the manner previously described, and an interior side (not labeled) is configured to be attached to the wrap 20 in a secured manner.

By providing the attachment system of the first attachment portion 210 and second attachment portion 220 in addition to the use of adhesives, the inventors have recognized that the sensing device 10 can be reattached many times with no degradation on the ability to fixate the sensing device 10 on the finger 9. In some examples, the adhesive 196 provided between the sensing device 10 and the finger 9 is configured to generally provide friction that resists translation and rotation of the sensing device 10 relative to the finger 9, whereas pressure on the finger 9 is adjustably provided through engagement of the first attachment portion 210 and second attachment portion 220.

Since the attachment system provided by the first attachment portion 210 and second attachment portion 220 need not adhere to the skin, durable and highly-reusable materials such as hook and loop fasteners may be incorporated, providing hundreds or even thousands of reuses to accommodate for pressure adjustments and the like. The first and second attachment portions 210, 220 also allow the patient to frequently remove the sensing device 10 for washing hands and the like. Particularly in light of COVID-19 pandemic, the inventors have recognized that the ability to enable frequent hand washing without discouraging the removable of the sensing device 10, or requiring frequent replacement thereof, is highly beneficial over systems presently known in the art. In short, the inventors have identified that the "sticky" type securement from adhesives, along with a non-adhesive secondary attachment system (the first and second attachment portions 210, 220) provide a combined benefit that is greater than the sum of these parts separately.

Remaining with FIGS. 2 and 3, the sensing device 10 includes a canopy 70 having an exterior side 20 facing away from the finger 9, and an interior side 74 towards the finger 9. The canopy 70 extends a length 71 and a width 73 such that an interior volume 80 is provided therein for retaining a portion of the electronics for operating the sensing device 10 discussed further below. In the example shown, an edge 82 of the canopy 70 is permanently or semi-permanently coupled to the wrap 20 in a water-tight manner via a weld region 83, which may be welded using laser welding or other types of welding known in the art. Other methods for attaching the canopy 70 to the wrap 20 include adhesives, or integral formation between the two, for example. The canopy 70 may be formed of a plastic or ceramic material, for example, to provide waterproofing and impact protection for the components retained therein. In certain embodiments, the canopy 70 is constructed of ABS plastic, polycarbonate, polyamide PA6, and/or polyamide PA66, for example.

In certain embodiments, the weld region 83 where canopy 70 meets the wrap 20 forms a transmissive border by which light generated within the canopy 70 is visible to the patient or caregiver from the outside. For example, the weld region 83 (which need not be welded, but is referred to for simplicity) may be made of polycarbonate, a clear acrylic, and/or fiberoptic material with light indicators 156 (FIG. 7, discussed below) positioned in sufficient proximity that a portion or the entire transmissive boarder glows.

In certain embodiments, the canopy 70 is removable (e.g., via a razor blade cutting the weld region 83) so as to provide service and/or replacement to the electronic components held therein, for example to replace batteries before returning the device to (new) service. In this manner, a new canopy 70 may then be re-adhered or re-welded to the wrap 20, which allows a single-use sensing device 10 to be refurbishable for many uses. In certain examples, other steps are also involved in the refurbishment process, including sterilization and the application of a new adhesive 196 for contacting the skin of a new patient and applying a new temporary backing sheet, for example.

The embodiment shown in FIG. 2 depicts light openings 86 provided within the canopy 70, which provide visibility to LEDs or other lights indicators (see 156 of FIG. 7) within the interior volume 80 of the canopy 70 to be seen outside of the sensing device 10. In particular, these light openings 86 may be used for communicating a status of a pairing process between the sensing device 10 and a central receiver 2, a power state, a communication state, or battery level for the sensing device 10, and/or provide indications as to the current SpO2 level being detected by the sensing device 10. For example, different colors may represent different states (green for high battery, yellow for medium, red for low), flashing and/or pulsing at different rates during the pairing process or other operations, or a combination of these features, for example.

Figure 6:
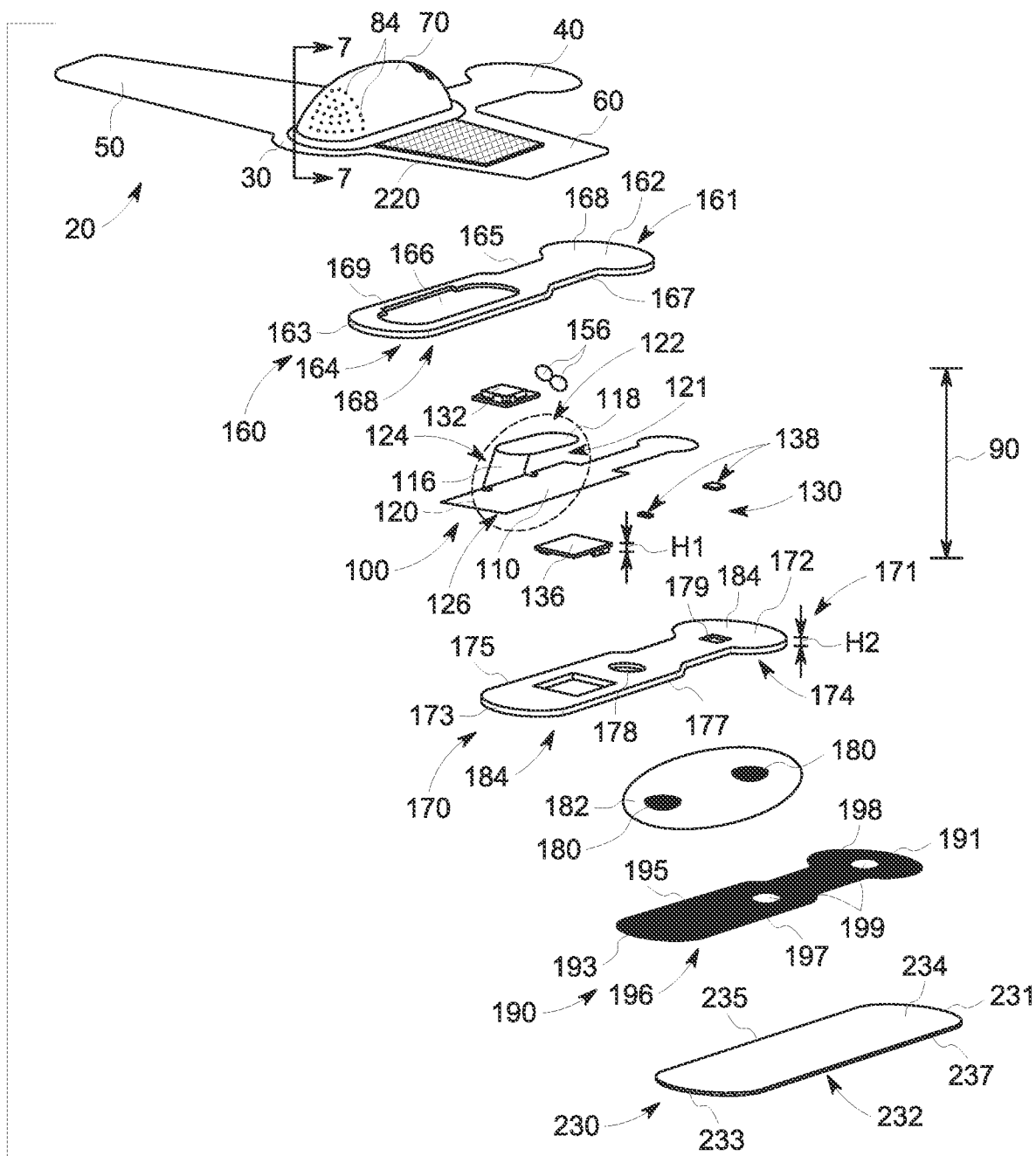
FIG. 6 is an exploded isometric view of an embodiment similar to that shown in FIG. 1 before attachment to a patient.

In the embodiment shown in FIG. 6, the canopy 70 further defines vent openings 84 therein, which in the present example allow for gas exchange between the interior volume 80 of the canopy 70 and the ambient air. In the case of using Zn-air batteries, which are discussed further below, these vent openings 84 also provide for necessary oxygen for the chemical reactions of these batteries, while still being defined sufficiently small so as to prevent moisture from entering the canopy 70 to damage electrical components therein. In particular, the inventors have recognized that vent openings 84 may be particularly sized such that heat and air flow may occur, but that the surface tension of water and other liquids prevents such moisture from passing through the vent openings 84.

Figure 4:
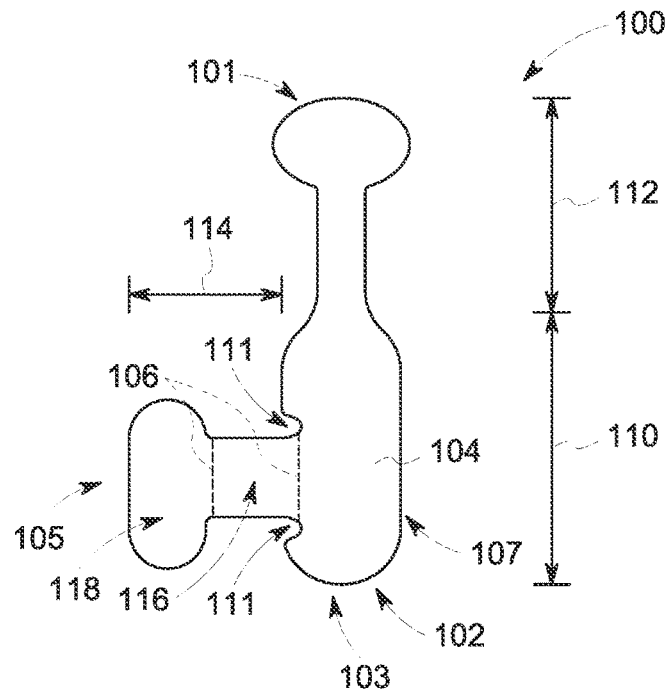
FIG. 4 is a top view of an exemplary carrier board as may be provided within the embodiments shown in FIGS. 1-3.

FIG. 4 depicts an exemplary carrier board 100 within the electronics system 90 (FIG. 6) for operating the sensing device 10. The carrier board 100 is shown in a flat configuration, before being formed and installed within the sensing device 10. In particular, the carrier board 100 has a central portion 110 configured to substantially align with the central portion 30 of the wrap 20. A tip extension 112 extends from the central portion 110 and is configured to substantially align with the tip wing 40 of the wrap 20. A side extension 114 comprising a connector 116 and shelf 118 extend from the central portion 110 as well, whereby the side extension 114 is configured to be folded or rolled into a stacked portion 120 (FIG. 6) to be discussed below. A notch 111 is formed in the central portion 110, serving as a strain relief for the side extension 114.

In the embodiment shown in FIG. 4, the tip extension 112 and the side extension 114 extend away from the central portion 110 at approximately 90° apart. In total, the carrier board 100 extended between the tip side 101 and a knuckle side 103, and between a left side 105 and a right side 107. As will be more apparent in view of the folded form shown in FIG. 6, the carrier board 100 has an exterior side 102 opposite an interior side 104. Fold lines 106 depict where the carrier board 100 of the present embodiment is folded or rolled as shown in FIG. 6. As will become apparent, the carrier board 100 is configured such that a power system 140 (FIG. 5) can be retained within the interior side 104 of the carrier board 100, specifically within the stacked portion 120.

Figure 5:
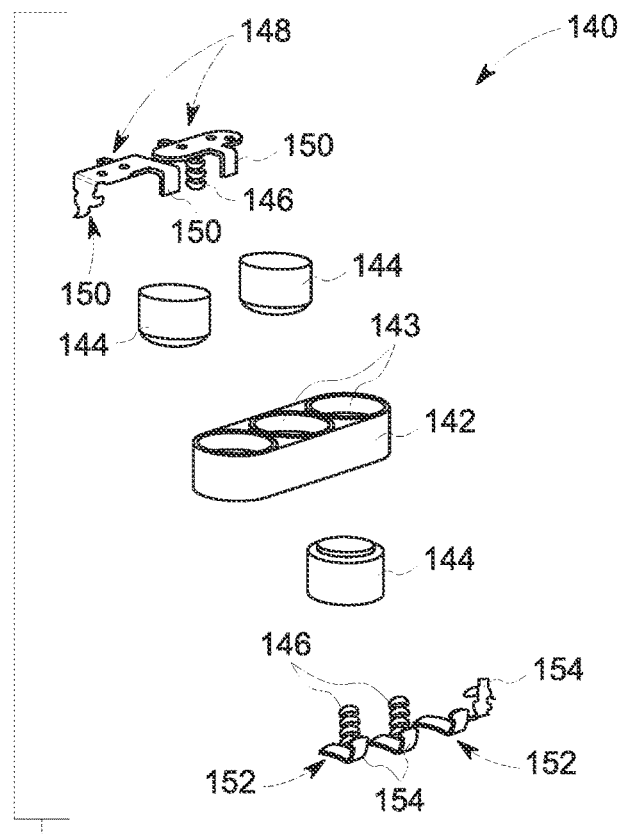
FIG. 5 is an exploded isometric view of a power system such as may incorporated within the embodiments of FIGS. 1-3.

FIG. 5 depicts an exemplary power system 140 such as may be incorporated within the electronics system 90 to power the sensing device 10. The power system 140 of FIG. 5 includes a housing 142 defining receivers 143 configured to receive one or more batteries 144. Springs 146 are provided such that the batteries 144 make contact with upper contacts 148 and lower contacts 152, which are anchored to the housing 142 via anchors 150, 154, respectively, in a manner presently known in the art. In certain embodiments, the housing 142 is made of a rigid material, such as plastic, to provide sufficient strength for supporting the springs 146, upper contacts 148, and lower contacts 152.

As discussed above and shown in FIG. 6, the power system 140 is configured to be received within a cavity 121 defined within the stacked portion 120, formed by virtue of folding the side extension 114 in the manner previously discussed. This provides for space savings due to the greater density of the electronic system 90, and also isolation between components within the electronics system as discussed below. The power system 140 is electrically coupled to the carrier board 100 in a manner known in the art.

FIG. 6 depicts the sensing device 10 as layers, which provide features and functionality described above, but also provides for efficient manufacturing and water-sealing for electrical components therein. The uppermost layer shown is the wrap 20 (including the canopy 70) previously discussed, which may include an adhesive on the underside of the central portion 30 for coupling to the next layer, in the present case is first sealing layer 160. It will be recognized that while the present example shows a first sealing layer 160 and a second sealing layer 170, greater or fewer sealing layers may be used, and thus different configurations are anticipated by the present disclosure. In certain embodiments, the sealing layers are made of a foam material. Exemplary materials for constructing the sealing layers include Vancive 2120U+3M1774W by Avery Dennison® and/or NMC TA-100+3M 1522 medical tape by 3M®.

In the example shown in FIG. 6, the first sealing layer 160 is configured to substantially overlap with the central portion 30 of the wrap 20. The first sealing layer 160 extends between tip side 161 and knuckle side 163 and left side 165 and right side 167. An exterior side 162 is configured to be coupled to the wrap, such as via an adhesive 168 on the first sealing layer 160, wrap, or both. A finger side 164 is opposite of the exterior side 162, which may also in certain embodiments be provided with an adhesive 168 for adhering to the carrier board 100, which may be the same or different from the adhesive on the exterior side 162 and/or on the wrap 20. The first sealing layer 160 defines an opening 166 therethrough, which in the present example includes a notch 169. This opening 166 is configured to receive at least a portion of the stacked portion 120 of the carrier board 100 therein. A notch 169 provided within the opening 166 of the first sealing layer 160 for generally aligning with the stacked portion 120 of the carrier board 100, thus enabling centering and alignment of the carrier board 100 and the first sealing layer 160.

Remaining with FIG. 6, the stacked portion 120 of the carrier board 100 is defined as having a canopy side 122, finger side 124, and connector side 126 therebetween. At least a portion of the stacked portion 120 is received within the canopy 70 by extending through the opening 166 in the first sealing layer 160. As previously discussed, the power system 140 (not presently shown) may be incorporated within the cavity 121 of the stacked portion 120. Additionally, a first circuit board 132 is electrically coupled to the carrier board 100 and positioned on the shelf 118 thereof. In this manner, the first circuit board 132 is also configured to be retained within the canopy 70 when assembled.

In certain examples, the carrier board 100 is single or double sided etched copper on polyimide (PI) film, approximately 0.2 mm thick, for example. In other examples, the carrier board 100 is formed of polyethylene (PET) or thermoplastic polyurethane (TPU). On which the traces may be printed, for example using silver ink.

In certain embodiments, the first circuit board 132 is configured to provide wireless connectivity between the sensing device 10 and central receiver 2. The first circuit board 132 includes a microcontroller unit (MCU), radio circuit (RFID), power management unit (PMU), and antenna. The electronics circuits may be separate or parts of a single silicon (e.g., nRF52), or packaged in a single hybrid component, for example. In certain examples, the first circuit board 132 is approximately 10 mm×10 mm and approximately 0.5 mm thick. The first circuit board 132 may be constructed of FR4 with etched copper tracings as known in the art, which may be 4 or 6 layers thick, for example. In certain examples the component pitch is tight, down to 0.4 mm. Large pads of approximately 1 mm thickness may be used on the non-component side for bonding the first circuit board 132 to the carrier board 100. Bonding between the first circuit board 132 and the carrier board 100 may be done by soldering (e.g., for PI) and/or conductive adhesives such as silver-epoxy or anisotropic conductive file (ACF) (e.g., for PET or TPU).

It will be recognized that these dimensions have been provided as merely exemplary and are not limitations on the present disclosure.

A second circuit board 136 is also electrically coupled to the carrier board 100. However, in contrast to the first circuit board 132 provided on the canopy side 122 of the stacked portion 120, the second circuit board 136 is coupled on the finger side 124 of the stacked portion 120. In certain embodiments, the second circuit board 136 is configured to control the optical components 138 and to process data received therefrom, which is further sent to the first circuit board 136. In certain embodiments, the second circuit board 136 includes analog front-end (AFE) and optical components. One such example of an AFE is an Analog Devices ADPD106 or AD80396 as known in the art, which includes LED drivers, amplifiers, and AD-converters. The AFE may communicate with the microcontroller unit (MCU) on the first circuit board 132 via serial data bus, such as SPI or I2C, for example.

It will be recognized that the specific configuration of components between the first circuit board 132 and second circuit board 136 is not fixed and may be configured in many ways. By way of providing another non-limiting example, the PMU, AFE, and MCU are located on the second circuit board 136, with the RFID and antenna being on the first circuit board 132. In certain examples, the RFIC is a hybrid including the MCU, RF, and antenna.

In further examples, a redundant MCU may be avoided by including the AFE on the second circuit board 136 and a single-chip MCU/RF on the first circuit board 132. The antenna may reside on the first circuit board 132, or may be implemented as part of other structures (for example, on the carrier board 100 or printed on the canopy 70). In this configuration, the PMU may reside on either of the first circuit board 132 or second circuit board 136 (the latter potentially providing improved measurement noise performance).

Also coupled on the exterior side 102 of the carrier board 100, though in the present example not within the stacked portion 120, are optical components 138 for transmitting and/or receiving light to detect SpO2 levels of the patient. In the example shown, the optical components 138 include a transmitter 137, and a separate receiver 139, which as previously discussed are configured to be positioned on opposing sides of the finger 9 in use such that light is transmitted therethrough. The optical components 138 may be chosen from among those presently known in the art, or others that transmit light, receive light, or both transmit and receive light, for example.

An exemplary transmitter 137 available in the market is the Osram SFH 7016. Likewise, an exemplary receiver 139 is the Osram BPW 34 S-Z or SFH 2200. However, it will be recognized that these optical components 138 are merely exemplary and that other optical components 138 are also anticipated by the present disclosure.

In certain embodiments, the carrier board 100 and one or more electrical components 130 coupled thereto are overmolded so as to protect the assembly, which may then serve as a replaceable subcomponent for refurbishment and the like.

As shown in the embodiment of FIG. 6, a second sealing layer 170 is provided below the carrier board 100, and in certain examples coupled thereto via an adhesive 184, which may be provided on the sealing layer 170 and/or on the carrier board 100. The second sealing layer 170 extends between a tip side 171 and a knuckle side 173, and between a left side 175 and a right side 177. The second sealing layer 170 is coupled to the carrier board 170, and in certain places directly to the finger side 164 of the first sealing layer 160, on its exterior side 172. A finger side 174 is opposite of the exterior side 172 and an opening 176 is defined through the second sealing layer 170. The opening 176 is configured to substantially receive the second circuit board 136 therein. In particular, the second circuit board 136 is defined as having a height H1, and in the embodiment shown the height H2 of the second sealing layer 170 is configured to be at least as great as the height H1 of the second circuit board 136. The inventors have chosen to provide a second sealing layer 170 having a height H2 at least as great as the height H1 of the second circuit board 136 such that the patient cannot feel any electronics extending from the finger side 124 of the second circuit board 136 when the sensing device 10 is positioned on the finger 9.

Sensor openings are also defined within the second sealing layer 170, in the present example a transmitter opening 178 in alignment with the transmitter 137 and a receiver opening 179 in alignment with the receiver 139. In the present example shown in FIG. 6, the heights of the transmitter 137 and receiver 139 are less than the height H1 of the second circuit board 136, and thus the height H1 of the second sealing layer 170 provides that the patient cannot feel the transmitter 137 and/or receiver 139 when the sensing device 10 is positioned on the finger 9. This allows the light transmitted from the transmitter 137 and received by the receiver 139 to pass through the second sealing layer 170 unimpeded. This configuration also provides for sealing out ambient light by the transmitter opening 178 and receiver opening 179 being defined within the material of the second sealing layer 170.

In the embodiment shown in FIG. 6, a protective layer is also provided to protect the integrity of the transmitter 137 and receiver 139, particularly as there is a direct transmitter opening 178 and receiver opening 179 through the second sealing layer 170. In the example shown, a coating 180 is provided on a base 182, which may be adhered to the finger side 174 of the second sealing layer 170 using an adhesive such as described above. In other examples, coatings 180 may be provided directly within the transmitter opening 178 and/or receiver opening 179, or in other words overlapping these openings. For example, drops of silicone may be positioned within the transmitter opening 178 and/or receiver opening 179 and serve as the coating 180 to provide protection without adversely impacting the transmitting of the transmitter 137, and the receiving by the receiver 139. In essence, the coating 180 provides protection for the transmitter 137 and receiver 139 from moisture, dust, and other damage. It will be recognized that in certain embodiments, a base 182 is not necessary, and the coatings 180 may be independent, such as being retained within the transmitter opening 178 and/or receiver opening 179 directly.

The embodiment of FIG. 6 includes an adhesive layer 190 below the second sealing layer 170, below the base 182 containing the coating 180 previously discussed. However, it will be recognized that the adhesive layer 90 and the second sealing layer 170 may be a single component, for example where the coatings 180 are positioned directly within the transmitter opening 178 and receiver opening 179, for example. In this case, the adhesive 184 on the finger side 174 of the second sealing layer 170 would be a skin-compatible adhesive (which in certain embodiments would not be as strong and/or permanent as an adhesive for bonding to another material layer, such as the adhesive layer 190).

In the example shown in FIG. 6, the adhesive layer 190 extends between a tip side 191 and a knuckle side 193, and also between a left side 195 and right side 197. An exterior side 192 of the adhesive layer 190 is configured to be coupled to the base 182 and/or second sealing layer 170, for example via an adhesive 198, which may be the same or different from adhesives used for coupling other layers. The adhesive layer 90 further includes a finger side 194 opposite the exterior side 192, which is configured to contact the skin of the finger 9. The finger side 194 is provided with a skin adhesive 196, which is biocompatible and configured to contact the skin of the finger 9 in a manner presently known in the art. In the embodiment shown in FIG. 6, openings 199 are provided through the adhesive layer 190 to provide unimpeded transmission of the transmitter 137 and receiver 139.

Figure 7:
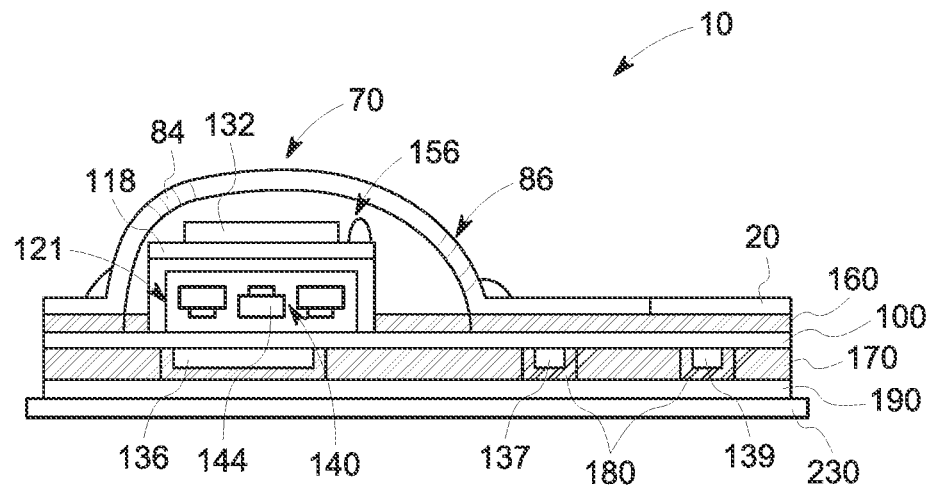
FIG. 7 is a sectional side view of an embodiment similar to that shown in FIG. 6, taken along the line 7-7 in FIG. 6.

In the embodiment of FIG. 6, the adhesive layer 190 is made of a dark color, which the inventors have identified to improve ambient light attenuation (thereby including openings 199 or transparent regions—at least with respect to the light produced by the transmitter 137—to allow transmission by the optical components 138). However, other embodiments according to the present disclosure provide for an adhesive layer 190 that is transparent or otherwise either does not impede transmission by the transmitter 137 or receiving by the receiver 139, or does so in a known and compensatable manner such that no openings 199 are needed through the adhesive layer 190. For example, the section view shown in FIG. 7 shows a sensing device 10 similar to that shown in FIG. 6, but having a transparent adhesive layer 190 such that no openings 199 are required for transmission and receipt of the light. Other configurations, including greater or fewer openings 199 or partially darkened portions of the adhesive layer 190 (e.g., surrounding the perimeter thereof) are also anticipated by the present disclosure.

Finally, FIG. 6 depicts a backing sheet 230 is releasably adhered to the finger side 194 of the adhesive layer 190, which is removed before attaching the sensing device 10 to the finger 9. The backing sheet 230 extends between a tip side 231 and a knuckle side 233, and between a left side 235 and a right side 237. The backing sheet 230 is temporarily coupled to the adhesive layer 90 on an interior side 234, also having an exterior side 232 opposite the interior side 234. In this manner, the backing sheet 230 may be peeled away from the adhesive layer 190 to expose the skin adhesive 196, allowing the sensing device 10 to be positioned on the patient's finger 9.

FIG. 7 shows a sectional side view of the embodiment shown in FIG. 6, now depicting the power system 140 in position within the cavity 121 formed within the carrier board 100. In the embodiment shown, light indicators 156, such as LEDs, are also provided on the canopy side 122 of the stacked portion 120 of the carrier board 100. As previously discussed, the light indicators 156 may provide differing colors, on/off states, or duty cycles to indicate different states for the sensing device 10.

Returning to the embodiment of FIG. 6, the inventors have configured the electronics 90 and carrier board 100 in this manner to provide additional benefits over devices presently known in the art. First, by forming the carrier board 100 in this manner, it is possible to attain efficiency and cost-savings by using a single-sided PCT, for example. Additionally, by separating the high-pitch (or high frequency) electronics into distinct, high-density boards that are electrically connected to the carrier board 100 (e.g., the first circuit board 132 and second circuit board 136), these devices may be separately built and tested before being assembled with the overall electronics system 90. Likewise, the wrap-around or folded construction of the carrier board 100 provides for separation of the high-frequency components (first circuit board 132 and second circuit board 136) to prevent or reduce interference or noise, while also shielding the analog electronics from ambient interference. Folding the carrier board 100 around the power system 140 also limits the folds to angles that will not overly strain the carrier board 100, preventing damage to electrical contacts therein, for example. Non-limiting examples of "analog electronics" include the second circuit board 136, optical components 138, and traces therebetween.

Likewise, in certain embodiments, the antenna 131 for wireless communication may be etched copper on PI, or printed silver on PET film positioned in close proximity to the first circuit board 132 atop the stacked portion 120 of the carrier board 100. This proximity of the RF electronics (within the first circuit board 132) avoids interference with the antenna 131, and likewise from the increased distance of the antenna 131 from the patient's skin. In other words, the sensing device 10 is optimized such that RF devices are far from the skin, and sensor devices are near the skin.

Figure 8:
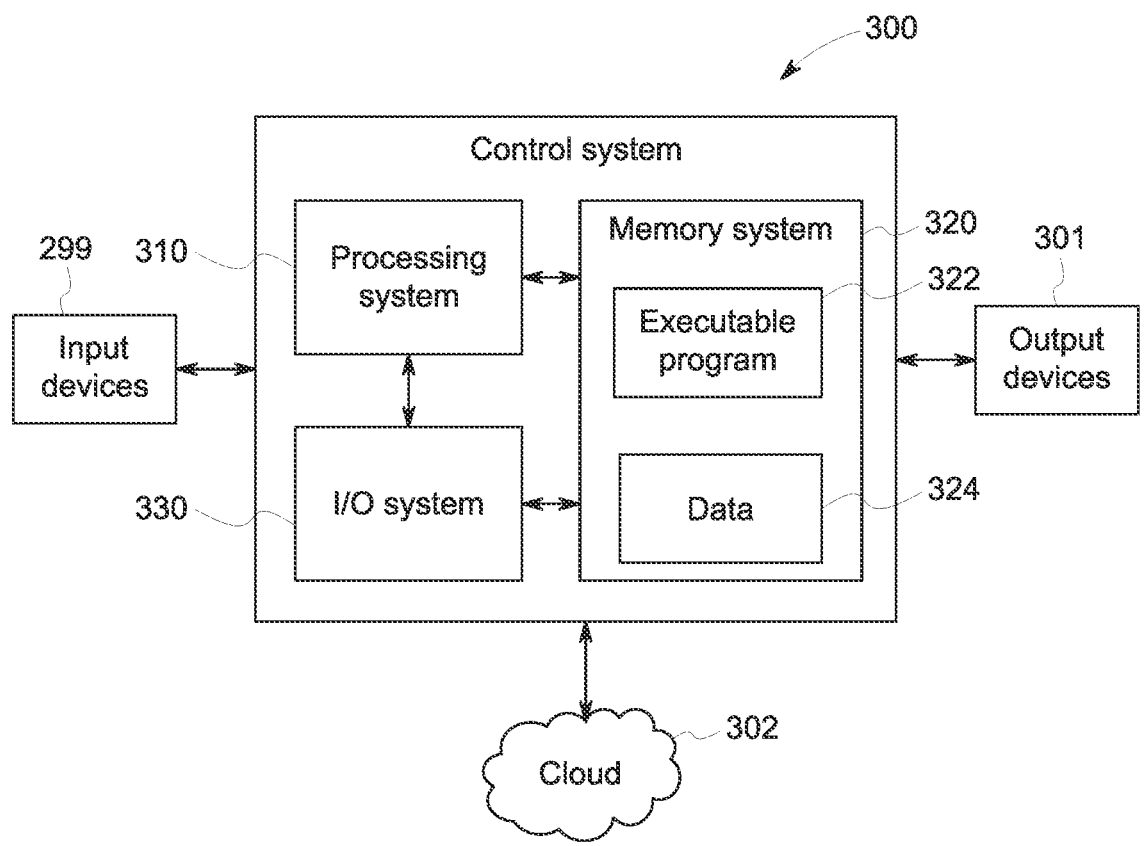
FIG. 8 is an exemplary control system as may be incorporated within the sensor device according to the present disclosure.

FIG. 8 depicts an exemplary control system 300 that may be incorporated within the sensing device 10 for performing the functions discussed above, which may be incorporated in part or whole within the first circuit board 132 and/or the second circuit board 136. It will be recognized that certain aspects of the present disclosure are described or depicted as functional and/or logical block components or processing steps, which may be performed by any number of hardware, software, and/or firmware components configured to perform the specified functions. For example, certain embodiments employ integrated circuit components, such as memory elements, digital signal processing elements, logic elements, look-up tables, or the like, configured to carry out a variety of functions under the control of one or more processors or other control devices. The connections between functional and logical block components are merely exemplary, which may be direct or indirect, and may follow alternate pathways.

In certain examples, the control system 300 communicates with each of the one or more other electrical components 130 of the sensing device 10 and the central receiver 2 via a communication link CL, which can be any wired or wireless link. The control system 300 is capable of receiving information and/or controlling one or more operational characteristics of the sensing device 10 and its various sub-systems by sending and receiving control signals via the communication links CL. In one example, the communication link CL is a controller area network (CAN) bus; however, other types of links could be used. It will be recognized that the extent of connections and the communication links CL may in fact be one or more shared connections, or links, among some or all of the components in the sensing device 10. Moreover, the communication link CL lines are meant only to demonstrate that the various control elements are capable of communicating with one another, and do not represent actual wiring connections between the various elements, nor do they represent the only paths of communication between the elements. Additionally, the sensing device 10 may incorporate various types of communication devices and systems, and thus the illustrated communication links CL may in fact represent various different types of wireless and/or wired data communication systems.

The control system 300 may be a computing system that includes a processing system 310, memory system 320, and input/output (I/O) system 330 for communicating with other devices, such as input devices 299 (e.g., the receiver 139 and/or wireless communication devices and the antenna 131 communicating with the first circuit board 132 and/or second circuit board 134) and output devices 301 (e.g., the transmitter 137, wireless communication devices, the antenna 131), either of which may also or alternatively be stored in a cloud 302. The processing system 310 loads and executes an executable program 322 from the memory system 320, accesses data 324 stored within the memory system 320, and directs the sensing device 10 to operate as described in further detail below.

The processing system 310 may be implemented as a single microprocessor or other circuitry, or be distributed across multiple processing devices or sub-systems that cooperate to execute the executable program 322 from the memory system 320. Non-limiting examples of the processing system include general purpose central processing units, application specific processors, and logic devices.

The memory system 320 may comprise any storage media readable by the processing system 310 and capable of storing the executable program 322 and/or data 324. The memory system 320 may be implemented as a single storage device, or be distributed across multiple storage devices or sub-systems that cooperate to store computer readable instructions, data structures, program modules, or other data. The memory system 320 may include volatile and/or non-volatile systems, and may include removable and/or non-removable media implemented in any method or technology for storage of information. The storage media may include non-transitory and/or transitory storage media, including random access memory, read only memory, magnetic discs, optical discs, flash memory, virtual memory, and non-virtual memory, magnetic storage devices, or any other medium which can be used to store information and be accessed by an instruction execution system, for example.

In this manner, the presently disclosed systems and methods provide for SpO2 sensor devices configured to be tightly fixed to a body part, which remaining lightweight, highly adjustable, recyclable, and providing other benefits over those known in the prior art.

This written description uses examples to disclose the invention, including the best mode, and also to enable any person skilled in the art to make and use the invention. Certain terms have been used for brevity, clarity, and understanding. No unnecessary limitations are to be inferred therefrom beyond the requirement of the prior art because such terms are used for descriptive purposes only and are intended to be broadly construed. The patentable scope of the invention is defined by the claims and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

What is claimed is:

1. A sensing device for acquiring data via a finger, the device comprising:
   a wrap having a central portion with a tip wing, a first side wing, and a second side wing each extending therefrom, wherein the wrap has an exterior side and an opposite finger side that faces towards the finger;
   an electronics system coupled to the wrap and having a sensor configured to acquire the data from the finger;
   an adhesive configured to adhere the sensing device to the finger; and
   first and second attachment portions positioned on finger side of the first side wing and on the exterior side of the second side wing, respectively, wherein the first and second attachment portions removably attach to each other to non-adhesively secure the wrap around the finger,
   wherein the central portion defines a central opening therein, and
   wherein the sensing device further comprises a canopy that extends upwardly from the exterior side of the central portion, wherein the canopy defines an interior volume accessible through the central opening in the central portion, and wherein the electronics system has a stacked portion that is at least partially positioned within the canopy.

2. The device according to claim 1, wherein the stacked portion of the electronics system has a canopy side facing the canopy, a finger side facing the finger, and a connector side between the canopy side and the finger side, further comprising a sealing layer with an finger side and an opposite exterior side and defining an sealing layer opening through which the canopy side of the electronics system extends.

3. The device according to claim 1, wherein the first attachment portion is a hook fastener and the second attachment portion is a loop fastener.

4. The device according to claim 1, wherein the wrap comprises an elastic material.

5. The device according to claim 1, further comprising an adhesive layer coupled to the wrap finger side of the wrap, wherein the adhesive configured to adhere the sensing device to the finger is positioned on the adhesive layer.

6. The device according to claim 5, further comprising a sealing layer positioned between the adhesive layer and the finger side of the wrap.

7. The device according to claim 5, wherein the stacked portion of the electronics system has a canopy side facing the canopy, a finger side facing the finger, and a connector side between the canopy side and the finger side, wherein the sensor extends away from the stacked portion on the finger side, further comprising a sealing layer positioned between the wrap and adhesive layer, wherein the sealing layer defines a sensor opening that aligns with at least a portion of the sensor normal to the finger.

8. The device according to claim 7, wherein the sealing layer includes foam to cushion the finger against contacting the electronics system.

9. The device according to claim 7, further comprising a coating positioned over the sensor opening to prevent moisture from passing therethrough.

10. The device according to claim 7, wherein the sensor comprises a transmitter and a receiver positioned apart from the transmitter, and wherein the sensor opening comprises a transmitter opening aligned with the transmitter and a receiver opening aligned with the receiver.

11. The device according to claim 10, wherein the device is configured such that when the wrap is secured around the finger the transmitter and the receiver are on aligned normal to the finger on opposite sides of the finger.

12. The device according to claim 5, wherein the adhesive layer is transparent.

13. The device according to claim 1, wherein the first side wing is longer than the second side wing, and wherein the second side wing is longer than the tip wing.

14. The device according to claim 1, wherein the canopy defines openings therein, wherein the openings are configured to allow gas exchange between the interior volume of the canopy and ambient air, and wherein the openings are configured such that surface tensions of liquids prevent the liquids from passing through the openings.

15. The device according to claim 1, wherein the canopy is configured such a light from the electronics system is visible therethrough.

16. The device according to claim 1, further comprising a transmissive border coupled between the wrap and the canopy, wherein the transmissive border is configured such a light from the electronics system illuminates at least a portion of the transmissive border.

17. The device according to claim 1, wherein the tip wing extends from the central portion at a 90 degree angle relative to both the first and second side wings, and wherein the first and second side wings are at a 180 degree relative to each other.

18. An $SpO_2$ sensing device securable on a finger, the $SpO_2$ sensing device comprising:
- an elastic wrap having a central portion with a central opening defined therein, wherein a tip wing, a first side wing, and a second side wing each extend from the central portion, and wherein the wrap has an exterior side and an opposite finger side facing towards the finger;
- a canopy extending upwardly from the exterior side of the central portion and defining an interior volume therein;
- a first sealing layer coupled to the interior side of both the central portion and tip wing, wherein an opening is defined through the first sealing layer;
- an electronics system having a canopy side facing the canopy, a finger side facing the finger, and a connector side between the canopy side and the finger side, wherein the electronics system extends through the opening in the first sealing layer and through the central opening in the wrap such that the canopy side is positioned within the canopy, wherein the electronics system further includes a carrier board and transmitter and a receiver that extend away from the carrier board towards the finger;
- a second sealing layer coupled to the carrier board of the electronics system, wherein openings are defined through the second sealing layer into which the transmitter and the receiver extend, respectively; and
- an adhesive layer coupled to the second sealing layer at an exterior side, the adhesive layer also having a finger side opposite the exterior side that has adhesive to retain the device on the finger; and
- first and second attachment portions positioned on finger side of the first side wing and on the exterior side of the second side wing, respectively, wherein the first and second attachment portions together comprises a hook and loop fastener removably attachable to secure the wrap around the finger.

* * * * *